United States Patent [19]

Aoki

[11] Patent Number: 5,780,664
[45] Date of Patent: Jul. 14, 1998

[54] AMMOXIDATION CATALYST COMPOSITION

[75] Inventor: Kunitoshi Aoki, Tokyo, Japan

[73] Assignee: Asahi Kasei Kogyo Kabushi Kaisha, Osaka, Japan

[21] Appl. No.: 583,028

[22] PCT Filed: Aug. 16, 1993

[86] PCT No.: PCT/JP94/01356

§ 371 Date: Sep. 12, 1996

§ 102(e) Date: Sep. 12, 1996

[87] PCT Pub. No.: WO95/05241

PCT Pub. Date: Feb. 23, 1995

[30] Foreign Application Priority Data

Aug. 17, 1993 [JP] Japan .................. 5-222745

[51] Int. Cl.$^6$ .................. B01J 21/08; B01J 21/12; B01J 27/192; C07C 253/26
[52] U.S. Cl. .................. 558/323; 502/212; 502/221; 502/246; 502/255; 502/259
[58] Field of Search .................. 502/212, 221, 502/246, 255, 259; 558/323

[56] References Cited

U.S. PATENT DOCUMENTS

| | | | |
|---|---|---|---|
| 3,746,657 | 7/1973 | Miller et al. | 252/437 |
| 4,123,453 | 10/1978 | Grasselli et al. | 260/465.3 |
| 4,139,552 | 2/1979 | Grasselli et al. | 260/465.3 |
| 4,162,234 | 7/1979 | Grasselli et al. | 252/432 |
| 4,192,776 | 3/1980 | Grasselli et al. | 252/432 |
| 4,228,098 | 10/1980 | Aoki et al. | 260/465.3 |
| 4,264,476 | 4/1981 | Umemura et al. | 252/458 |
| 4,290,922 | 9/1981 | Umemura et al. | 252/456 |
| 4,443,556 | 4/1984 | Aoki et al. | 502/212 |
| 4,541,964 | 9/1985 | Katsumata et al. | 260/465.3 |
| 4,600,541 | 7/1986 | Aoki et al. | 558/321 |
| 4,624,800 | 11/1986 | Sasaki et al. | 252/313.2 |
| 4,965,393 | 10/1990 | Sasaki et al. | 558/324 |
| 5,071,814 | 12/1991 | Sasaki et al. | 502/205 |
| 5,093,299 | 3/1992 | Suresh et al. | 502/212 |

FOREIGN PATENT DOCUMENTS

| | | |
|---|---|---|
| 0 265 964 A2 | 5/1988 | European Pat. Off. . |
| 0 437 056 A2 | 7/1991 | European Pat. Off. . |
| 0 464 289 B1 | 1/1992 | European Pat. Off. . |
| 54-12913 | 5/1979 | Japan . |
| 55-10534 | 3/1980 | Japan . |
| 61-158810 | 7/1986 | Japan . |
| 63-285112 | 11/1988 | Japan . |
| 5-85718 | 4/1993 | Japan . |

*Primary Examiner*—Johann Richter
*Assistant Examiner*—Jane C. Oswecki
*Attorney, Agent, or Firm*—Pennie & Edmonds LLP

[57] ABSTRACT

Disclosed is an ammoxidation catalyst composition for use in producing acrylonitrile from propylene, or methacrylonitrile from isobutylene, by ammoxidation of the propylene or of the isobutylene, comprising an oxide catalyst and a silica carrier having the oxide catalyst supported thereon, wherein the silica carrier is present in an amount of from 40 to 60% by weight, based on the total weight of the oxide catalyst and the silica carrier. The oxide catalyst comprises oxides of molybdenum, bismuth, iron, and component A which is at least one element selected from potassium, rubidium and cesium, wherein bismuth, iron and component A are, respectively, present in amounts of from 0.1 to 6, from 0.1 to 8 and from 0.01 to 0.5 in terms of atomic ratios relative to twelve atoms of molybdenum. The ammoxidation catalyst composition is prepared by providing a slurry comprised of a silica sol and sources of component metallic elements of the oxide catalyst, and spray-drying the slurry, followed by calcination, wherein the silica sol has an aluminum content of 0.04 or less in terms of an atomic ratio relative to 100 atoms of silicon. By use of the catalyst composition of the present invention, the selectivity for acrylonitrile or methacrylonitrile can be significantly improved.

4 Claims, No Drawings

AMMOXIDATION CATALYST COMPOSITION

BACKGROUND OF THE INVENTION

1. Technical field

The present invention relates to a catalyst composition for use in ammoxidation of propylene or isobutylene in the gaseous phase. More particularly, the present invention is concerned with an ammoxidation catalyst composition comprising an oxide catalyst and a silica carrier having the oxide catalyst supported thereon, the oxide catalyst comprising oxides of molybdenum, bismuth, iron, and at least one element selected from potassium, rubidium and cesium, wherein bismuth, iron and the at least one element are present in specific proportions, the ammoxidation catalyst composition being one which has been prepared using as a source of silica a silica sol having an extremely low content of aluminum. When the ammoxidation catalyst composition of the present invention is used in producing acrylonitrile from propylene, or methacrylonitrile from isobutylene, on a commercial scale, the desired acrylonitrile or methacrylonitrile can be produced with high selectivity.

2. Prior art

There has been well known a process for producing acrylonitrile from propylene, or methacrylonitrile from isobutylene, by gaseous-phase ammoxidation of the propylene or of the isobutylene, which comprises reacting propylene with, or reacting isobutylene with ammonia and a molecular oxygen-containing gas. This process, which has been widely known as an ammoxidation process, has been practiced on a commercial scale. With respect to catalysts for use in this ammoxidation process and methods for preparing the same, a number of proposals have been made, wherein the catalysts have compositions containing molybdenum, bismuth and iron.

For example, in U.S. Pat. No. 4,965,393, U.S. Pat. No. 5,071,814, U.S. Pat. No. 4,192,776, Examined Japanese Patent Application Publication No. 54-12913, U.S. Pat. Nos. 4,123,453, 3,746,657, 4,264,476, 4,228,098, 4,290,922, 4,139,552, 4,162,234, 4,443,556, 4,600,541 and 5,093,299, oxide catalysts and methods for producing the same are disclosed wherein the oxide catalysts have multi-component compositions containing molybdenum, bismuth and iron.

In all of the above patent documents, the oxide catalyst is supported on a silica carrier and, in a method for producing such an oxide catalyst, a silica sol is used as a source of silica. However, with respect to the purity of the silica sol, no description is found in those patent documents.

DISCLOSURE OF THE INVENTION

With respect to an ammoxidation catalyst composition for use in ammoxidation of propylene or isobutylene, comprising an oxide catalyst comprised of oxides of molybdenum, bismuth, iron, and at least one element selected from potassium, rubidium and cesium, and a silica carrier having the oxide catalyst supported thereon, the present inventors have made extensive and intensive studies on physical and chemical properties of a silica sol to be used as a source of the silica. As a result, it has been found that by use of a catalyst composition prepared using a high purity silica sol having an extremely low content of aluminum as an impurity, the desired acrylonitrile or methacrylonitrile can be produced with high selectivity. The present invention has been completed based on this novel finding.

Accordingly, it is an object of the present invention to provide an improved ammoxidation catalyst composition comprising an oxide catalyst and a silica carrier having the oxide catalyst supported thereon, the oxide catalyst composition comprising oxides of molybdenum, bismuth, iron, and component A which is at least one element selected from potassium, rubidium and cesium, which ammoxidation catalyst composition, when used for producing acrylonitrile from propylene, or methacrylonitrile from isobutylene on a commercial scale, is capable of producing the desired acrylonitrile or methacrylonitrile with high selectivity.

It is another object of the present invention to provide a process for producing acrylonitrile from propylene, or methacrylonitrile from isobutylene, using the above-mentioned improved ammoxidation catalyst composition.

The foregoing and other objects, features and advantages of the present invention will be apparent from the following detailed description and appended claims.

DETAILED DESCRIPTION OF THE INVENTION

In one aspect of the present invention, there is provided an ammoxidation catalyst composition for use in producing acrylonitrile from propylene, or methacrylonitrile from isobutylene, by ammoxidation of the propylene or of the isobutylene, comprising an oxide catalyst and a silica carrier having the oxide catalyst supported thereon, wherein the silica carrier is present in an amount of from 40 to 60% by weight, based on the total weight of the oxide catalyst and the silica carrier. The oxide catalyst comprises oxides of molybdenum, bismuth, iron, and component A which is at least one element selected from potassium, rubidium and cesium, wherein bismuth, iron and component A are, respectively, present in amounts of from 0.1 to 6, from 0.1 to 8 and from 0.01 to 0.5 in terms of atomic ratios relative to twelve atoms of molybdenum. The ammoxidation catalyst composition is prepared by providing a slurry comprised of a silica sol and sources of component metallic elements of the oxide catalyst, and spray-drying the slurry, followed by calcination, wherein the silica sol has an aluminum content of 0.04 or less in terms of an atomic ratio relative to 100 atoms of silicon.

The ammoxidation catalyst composition of the present invention, comprising an oxide catalyst and a silica carrier having the oxide catalyst supported thereon, has an essential feature in that the ammoxidation catalyst composition is one which has been prepared using as a source of silica a silica sol having an aluminum content of 0.04 or less, preferably 0.02 or less, in terms of an atomic ratio relative to 100 atoms of silicon.

The silica sol, which is used for the ammoxidation catalyst composition of the present invention, can be selected, without any particular limitation, from high purity silica sols obtained by various production methods, as long as the content of aluminum which is present as an impurity in the silica sol is not greater than the above-mentioned upper limit as defined in the present invention. With respect to a method for producing a silica sol of high purity, reference can be made to, for example, U.S. Pat. No. 4,624,800, Unexamined Japanese Patent Application Laid-Open Specification Nos. 61-158810 and 63-285112, EP 464289, Unexamined Japanese Patent Application Laid-Open Specification No. 5-85718 and Examined Japanese Patent Application Publication No. 55-10534.

When the content of aluminum as an impurity in the silica sol is more than 0.04, the selectivity for acrylonitrile or methacrylonitrile is lowered.

In the ammoxidation catalyst composition of the present invention comprising an oxide catalyst supported on a silica carrier, the oxide catalyst contains molybdenum, bismuth, iron and component A (which is at least one element selected from potassium, rubidium and cesium) as essential component metallic elements. In addition to those essential component metallic elements, the oxide catalyst may optionally contain cobalt, nickel, manganese, magnesium, zinc, chromium, indium, cerium, praseodymium, neodymium, phosphorus, sodium, lithium, silver, thallium, calcium, strontium, barium, lead, lanthanum, samarium, gadolinium, gallium, zirconium, vanadium, niobium, tungsten, antimony, tellurium, palladium, platinum, osmium, iridium and/or the like. Especially, it is preferred that the catalyst composition contain at least one element selected from cobalt and nickel in an amount of 10 or less in terms of an atomic ratio relative to 12 atoms of molybdenum, and at least one element selected from manganese, magnesium, zinc, chromium, indium, cerium, praseodymium, neodymium, phosphorus and sodium in an amount of 3 or less in terms of an atomic ratio relative to 12 atoms of molybdenum. With such a catalyst composition, not only can the selectivity for acrylonitrile or methacrylonitrile be improved, but also the reactivity of propylene or isobutylene and the properties of the catalyst (such as surface area, pore distribution, particle morphology and density) can be easily and appropriately adjusted. In the present invention, for convenience' sake, phosphorus is described as belonging to the category of metallic elements.

The ammoxidation catalyst composition of the present invention can be produced by substantially the same method as disclosed in, for example, Examined Japanese Patent Application Publication No. 54-12913 or Examined Japanese Patent Application Publication No. 57-49253, except that a silica sol having high purity is used. More specifically, the ammoxidation catalyst composition of the present invention can be produced by a method comprising the three steps of (1) preparing a slurry of starting materials containing a silica sol and the above-mentioned component metallic elements of the oxide catalyst, (2) spray-drying the slurry thus prepared to obtain a dried catalyst precursor, and (3) subjecting the dried catalyst precursor to calcination.

In step (1) of preparing a slurry of starting materials containing a silica sol and component metallic elements of the oxide catalyst, a silica sol having a silica content of from 10 to 50% by weight, preferably from 20 to 40% by weight, is used. With respect to the sources of the component metallic elements, there is no particular limitation as long as each of the elements is present in such a form as is soluble or dispersible in water or an aqueous solution of acid, such as nitric acid. Preferably, each of the component metallic elements is present in the form of a salt which is soluble in water or an aqueous solution of acid, such as nitric acid. Preferred examples of sources of elements include an ammonium salt, a nitrate, a chloride, a sulfate and an organic acid salt thereof. More specifically, it is preferred that as a molybdenum source, ammonium heptamolybdate be used, and that each of bismuth, iron, potassium, rubidium and cesium be used in the form of a nitrate. With respect to the sources of cobalt, nickel, manganese, magnesium, zinc, chromium, indium, cerium, praseodymium, neodymium and sodium, each of these elements may be present in the form of a nitrate. When it is intended to incorporate phosphorus in the oxide catalyst, phosphoric acid can be advantageously used as the source of phosphorus.

A slurry of starting materials can be prepared, for example, as follows: phosphoric acid is first added to a silica sol when the incorporation of phosphorus is intended, and an aqueous solution of ammonium heptamolybdate is then added to the resultant mixture, followed by addition of an aqueous solution of a mixture of nitrates of the remaining component metallic elements, wherein each addition is conducted while stirring.

In step (2) of spray-drying the slurry prepared in step (1) above, the spray-drying of the slurry can be generally conducted by centrifugation or two-phase flow nozzle method which has been commercially employed, to obtain a dried catalyst precursor. In this instance, it is preferred to use, for example, air which has been heated by indirect contact with steam and/or by using an electric heater, as a heat source for drying. The temperature of the spray dryer at an entrance thereof is preferably 300° C. or less, more preferably from 150° to 250° C.

Preferably, the dried catalyst precursor is subjected to a denitrification treatment before calcination. The denitrification treatment can be conducted at a temperature of from 350 to 450° C. for 0.5 to 2.0 hours.

In step (3) of calcination, for example, the dried denitrified catalyst precursor obtained above is calcined at a temperature of from 500 to 750° C., preferably from 550° to 720° C., to thereby obtain a desired oxide catalyst composition. The obtained catalyst composition is a crystalline catalyst composition containing various molybdates which are individually formed from molybdenum oxide and an oxide of each of the component metallic elements, such as bismuth and iron. When the dried denitrified catalyst precursor is calcined at 750° C. or more, the molybdates in the resultant catalyst composition may become amorphous.

When the calcination temperature is too low, although the conversion of propylene or isobutylene becomes high, the selectivity for acrylonitrile or methacrylonitrile becomes low. On the other hand, when the calcination temperature is too high, not only does the conversion of propylene or isobutylene become low, but combustion of ammonia is also likely to occur vigorously in the ammoxidation of propylene or isobutylene. Therefore, in the present invention, it is advantageous that the calcination temperature be in the above-mentioned range of from 500 to 750° C. It is also advantageous that the calcination time be in the range of from 1 to 5 hours. For selecting the most preferred calcination temperature and calcination time, it is desired to conduct experiments in which ammoxidation reactions are performed using catalyst compositions which have been prepared under various calcination conditions, thereby determining the most preferred calcination temperature and calcination time with reference to the results of the experiments, such as the conversion of propylene or isobutylene and the combustion ratio of ammonia.

Propylene, or isobutylene and ammonia to be used in the process of the present invention need not necessarily be of very high purity but may be of a commercial grade. Tert-butanol can also be advantageously used instead of isobutylene. As a source of an oxygen-containing gas, air is usually employed. Water may be added to a gaseous mixture of raw materials for the purpose of suppressing the combustion of ammonia. However, the addition of water is not essential, because water is produced in the ammoxidation reaction.

In the process of the present invention, it is advantageous that the volume ratios of propylene or isobutylene: ammonia: air be in the range of 1 : 0.9 to 1.4 : 7 to 11, preferably 1 : 1.0 to 1.3 : 8 to 10. The reaction temperature may be from 400° to 500° C., preferably from 420° to 470° C. The reaction may usually be conducted under a pressure of from atmospheric pressure to a pressure of 3 atm. The time of contact between a gaseous mixture of raw materials and the catalyst composition (contact time) may be from 1 to 8 seconds, preferably from 2 to 6 seconds. The process for producing acrylonitrile or methacrylonitrile by reacting propylene or isobutylene with a molecular oxygen-containing gas and ammonia in the presence of an ammoxidation catalyst composition of the present invention may be conducted using either a fluidized bed or a fixed bed as a catalyst bed. However, the use of a fluidized bed is more suitable for the ammoxidation catalyst composition of the present invention.

Thus, in another aspect of the present invention, there is provided a process for producing acrylonitrile or methacrylonitrile, which comprises reacting propylene or isobutylene with ammonia and a molecular oxygen-containing gas in the gaseous phase in the presence of an ammoxidation catalyst composition comprising an oxide catalyst and a silica carrier having the oxide catalyst supported thereon. The silica carrier is present in an amount of from 40 to 60% by weight, based on the total weight of the oxide catalyst and the silica carrier, and the oxide catalyst comprises oxides of molybdenum, bismuth, iron, and component A which is at least one element selected from potassium, rubidium and cesium, wherein bismuth, iron and component A are, respectively, present in amounts of from 0.1 to 6, from 0.1 to 8 and from 0.01 to 0.5 in terms of atomic ratios relative to twelve atoms of molybdenum. The ammoxidation catalyst composition is prepared by providing a slurry comprised of a silica sol and sources of component metallic elements of the oxide catalyst, and spray-drying the slurry, followed by calcination, wherein the silica sol has an aluminum content of 0.04 or less in terms of an atomic ratio relative to 100 atoms of silicon.

BEST MODE FOR CARRYING OUT THE INVENTION

Hereinbelow, the present invention will be described in more detail with reference to the following Examples, Comparative Examples and Reference Examples, but they should not be construed as limiting the scope of the present invention.

Reference Example (Preparation of a silica sol)

A mass of metallic silicon having an aluminum content of 0.015 in terms of an atomic ratio relative to 100 atoms of silicon was pulverized into particles having a particle size of 100 Tyler mesh-pass. The metallic silicon particles were maintained in a dryer at 120° C. for 20 hours. 1,000 g of the resultant dried metallic silicon particles were added to 4,000 g of hot water to obtain a mixture. While maintaining the temperature of the obtained mixture at 60° C., the mixture was stirred for 20 minutes and then, allowed to stand, to thereby form a supernatant. The supernatant was removed from the mixture. The above treatment of the metallic silicon particles with hot water was repeated two more times, to thereby obtain an aqueous slurry of metallic silicon. 5,900 g of a 0.5 wt % aqueous solution of sodium hydroxide was placed in a reactor having an agitator, a reflux condenser and a thermometer. The above-obtained slurry was added to the aqueous solution of sodium hydroxide and a reaction was conducted, while stirring, at 60° C. for 6 hours. After completion of the reaction, the resultant reaction mixture was cooled to room temperature and then, unreacted metallic silicon was removed by filtration. (The above operation was conducted in substantially the same manner as described in Example 2 of Examined Japanese Patent Application Publication No. 55-10534, except that the aluminum content of the metallic silicon used is different.) Thus, a sodium-containing silica sol was obtained. The sodium-containing silica sol was passed through 1.4 liters of "AMBERLITE IR-120" exchange resin (ammonia-type strongly acidic cation exchange resin manufactured and sold by Rohm & Haas Co., USA), to thereby obtain about 6,100 g of silica sol E-1 having a $SiO_2$ content of 29% by weight.

Substantially the same procedure as mentioned above was repeated to obtain silica sol E-2 and comparative silica sol C-1, except that the aluminum contents of the metallic silicon masses used for E-2 and C-1 were, respectively, 0.032 and 0.065, each in terms of an atomic ratio relative to 100 atoms of silicon. In a series of experiments described below as Examples 1 to 9 and Comparative Examples 1 to 9 (production of catalyst compositions), in addition to the above-mentioned three types of silica sols E-1, E-2 and C-1, two types of comparative silica sols, namely, a silica sol having an aluminum content of 0.068 ("LUDOX AS" silica sol; manufactured and sold by DuPont Co., USA) as comparative silica sol C-2, and a silica sol having an aluminum content of 0.31 ("SNOWTEX N" silica gel; manufactured and sold by Nissan Chemical Industries, Ltd., Japan) as comparative silica sol C-3 were used. The respective silica contents and aluminum contents of those 5 types of silica sols are shown in Table 1.

TABLE 1

|  | Silica Sol | $SiO_2$ (wt. %) | 100 × Al/Si (atomic ratio) |
| --- | --- | --- | --- |
| Examples | E-1 | 29 | 0.015 |
|  | E-2 | 30 | 0.032 |
| Comparative | C-1 | 29 | 0.065 |
| Examples | C-2: LUDOX AS | 40 | 0.068 |
|  | C-3: SNOWTEX N | 20 | 0.31 |

Examples 1 to 9 and Comparative Examples 1 to 9 (Production of catalyst compositions)

In Example 1, catalyst composition 1, composed of an oxide catalyst supported on 50% by weight, based on the total weight of the oxide catalyst and a silica carrier, of the silica carrier, having a structure represented by the formula: $Mo_{12}Bi_{4.0}Fe_{6.5}K_{0.08}P_{1.0}O_x$, was prepared as follows.

3.54 g of a 85 wt % aqueous solution of phosphoric acid was added to 345 g of silica sol E-1 while stirring, to obtain a mixture. To the thus obtained mixture was added a solution of 65.6 g of ammonium heptamolybdate $[(NH_4)_6Mo_7O_{24}\cdot 4H_2O]$ in 200 g of water.

To the resultant mixture was added a solution of 59.9 g of bismuth nitrate $[Bi(NO_3)_3\cdot 5H_2]$, 81.5 g of iron nitrate $[Fe(NO_3)_3\cdot 9H_2O]$ and 0.25 g of potassium nitrate $[KNO_3]$ in 110 g of a 13 wt % aqueous solution of nitric acid, to thereby obtain a slurry. The slurry thus obtained was fed to a centrifugation type spray-drying apparatus, in which the slurry was atomized by means of a sprayer having a dish type rotor disposed above the central portion of a dryer of the spray-drying apparatus, and dried while maintaining the entrance temperature of the dryer at 250° C. and the exit temperature of the dryer at 130° C., to thereby obtain a dried particulate catalyst precursor. The obtained dried particulate catalyst precursor was transferred to a kiln, in which the catalyst precursor was denitrified at 400° C. for 1 hour and then calcined at 690° C. for 2 hours, thereby obtaining a catalyst composition having an oxide catalyst supported on a silica carrier.

In Examples 2 to 9 and Comparative Examples 1 to 9, catalyst compositions 2 to 9 and catalyst compositions 11 to 9', respectively, each composed of an oxide catalyst supported on 50% by weight, based on the total weight of the oxide catalyst and a silica carrier, of the silica carrier, having the respective compositions indicated in Table 2, were individually prepared in substantially the same manner as in Example 1. In preparing of catalyst compositions 2 to 9 and 1' to 9', with respect to the sources of molybdenum, bismuth, iron, potassium and phosphorus the same materials as used for preparing catalyst composition 1 were used. When it was intended to incorporate rubidium, cesium, cobalt, nickel, manganese, magnesium, zinc, chromium, indium, cerium, praseodymium, neodymium and/or sodium in the catalyst compositions, rubidium nitrate $|RbNO_3|$, cesium nitrate $|CsNO_3|$, cobalt nitrate $|Co(NO_3)_2 \cdot 6H_2O|$, nickel nitrate $|Ni(NO_3)_2 \cdot 6H_2O|$, manganese nitrate $|Mn(No_3)_2 \cdot 6H_2O|$, magnesium nitrate $|Mg(NO_3)_2 \cdot 6H_2O|$, zinc nitrate $|Zn(NO_3)_2 \cdot 6H_2O|$, chromium nitrate $|Cr(NO_3)_3 \cdot 9H_2O|$, indium nitrate $|In(NO_3)_3 \cdot 3H_2O|$, cerium nitrate $|Ce(NO_3)_3 \cdot 6H_2O|$, praseodymium nitrate $|Pr(NO_2)_3 \cdot 6H_2O|$, neodymium nitrate $|Nd(NO_3)_3 \cdot 6H_2O|$ and sodium nitrate $|NaNO_3|$ were used as the sources of those elements. As silica sols E-1, E-2, C-1, C-2 and C-3, those which are indicated in Table 1 were, respectively, used. In preparing all catalyst compositions, denitrification was conducted at 400° C. for 1 hour before calcination. The calcination temperatures were varied within the range of from 560° to 700° C., as indicated in Table 2. The calcination time was 2 hours.

evaluated using three indices, namely, conversion of propylene, selectivity for acrylonitrile and acrylonitrile yield as defined by the following formulae. The values of those indices are shown in Table 3.

$$\text{Conversion } (c) \text{ of Propylene} = \frac{\text{mole of propylene reacted}}{\text{mole of propylene fed}} \times 100$$

$$\frac{\text{Selectivity } (s)}{\text{for Acrylonitrile}} = \frac{\text{mole of acrylonitrile formed}}{\text{mole of propylene reacted}} \times 100$$

$$\text{Acrylonitrile Yield } (s) = \frac{\text{mole of acrylonitrile formed}}{\text{mole of propylene fed}} \times 100$$

Using catalyst compositions 2 to 9 and catalyst compositions 1' to 9', respectively (exclusive of catalyst compositions 3 and 4') individually, ammoxidation reactions of propylene were conducted in substantially the same manner as in Example 10. In each of the reactions, the content of propylene in the gaseous mixture of raw materials was fixed to 9% by volume, and the volume ratio of propylene: ammonia was fixed to 1:1.2. The volume ratio of propylene : oxygen was selected within the range of 1 : 1.8 to 1.9. The reaction temperature and the contact time were varied, depending on the reactivity of the catalyst composition used.

TABLE 2

| Catalyst composition No. | Silica sol used | Calcination temperature (°C.) | Catalyst composition SiO₂ | | Catalyst composition Atomic ratios | | | | |
|---|---|---|---|---|---|---|---|---|---|
| | | | wt % | 100 × Al/Si | Mo | Bi | Fe | K, Rb, Cs | Others |
| Example 1 | 1 | E-1 | 690 | 50 | 0.015 | 12 | 4.0 | 6.5 | $K_{0.08}$ | $P_{1.0}$ |
| Example 2 | 2 | E-2 | 690 | 50 | 0.032 | 12 | 4.0 | 6.5 | $K_{0.08}$ | $P_{1.0}$ |
| Comp. Ex. 1 | 1' | C-1 | 690 | 50 | 0.065 | 12 | 4.0 | 6.5 | $K_{0.08}$ | $P_{1.0}$ |
| Comp. Ex. 2 | 2' | C-2 | 690 | 50 | 0.068 | 12 | 4.0 | 6.5 | $K_{0.08}$ | $P_{1.0}$ |
| Comp. Ex. 3 | 3' | C-3 | 690 | 50 | 0.31 | 12 | 4.0 | 6.5 | $K_{0.08}$ | $P_{1.0}$ |
| Example 3 | 3 | E-1 | 670 | 50 | 0.015 | 12 | 3.5 | 6.0 | $K_{0.3}Rb_{0.02}$ | $P_{1.0}$ |
| Comp. Ex. 4 | 4' | C-3 | 670 | 50 | 0.31 | 12 | 3.5 | 6.0 | $K_{0.3}Rb_{0.02}$ | $P_{1.0}$ |
| Example 4 | 4 | E-1 | 700 | 50 | 0.015 | 12 | 3.5 | 6.5 | $K_{0.08}$ | $P_{0.8}Na_{1.0}$ |
| Example 5 | 5 | E-1 | 700 | 50 | 0.015 | 12 | 2.5 | 6.5 | $K_{0.08}$ | $P_{0.3}Na_{1.0}Ce_{0.5}$ |
| Comp. Ex. 5 | 5' | C-3 | 700 | 50 | 0.31 | 12 | 2.5 | 6.5 | $K_{0.08}$ | $P_{0.3}Na_{1.0}Ce_{0.5}$ |
| Example 6 | 6 | E-1 | 570 | 50 | 0.015 | 12 | 1.0 | 2.5 | $K_{0.1}$ | $Co_{4.5}Ni_{2.5}$ |
| Comp. Ex. 6 | 6' | C-1 | 570 | 50 | 0.065 | 12 | 1.0 | 2.5 | $K_{0.1}$ | $Co_{4.5}Ni_{2.5}$ |
| Comp. Ex. 7 | 7' | C-3 | 570 | 50 | 0.31 | 12 | 1.0 | 2.5 | $K_{0.1}$ | $Co_{4.5}Ni_{2.5}$ |
| Example 7 | 7 | E-1 | 560 | 50 | 0.015 | 12 | 1.0 | 1.7 | $K_{0.1}$ | $Co_{4.5}Ni_{2.5}Mn_{0.5}Mg_{0.5}Zn_{0.2}$ |
| Example 8 | 8 | E-1 | 570 | 50 | 0.015 | 12 | 1.0 | 1.7 | $Cs_{0.04}$ | $Co_{4.5}Ni_{2.5}Cr_{0.5}In_{0.3}$ |
| Comp. Ex. 8 | 8' | C-3 | 570 | 50 | 0.31 | 12 | 1.0 | 1.7 | $Cs_{0.04}$ | $Co_{4.5}Ni_{2.5}Cr_{0.5}In_{0.3}$ |
| Example 9 | 9 | E-1 | 580 | 50 | 0.015 | 12 | 0.5 | 2.5 | $Rb_{0.05}$ | $Co_{4.5}Ni_{2.5}Pr_{0.2}Nd_{0.3}$ |
| Comp. Ex. 9 | 9' | C-3 | 580 | 50 | 0.31 | 12 | 0.5 | 2.5 | $Rb_{0.05}$ | $Co_{4.5}Ni_{2.5}Pr_{0.2}Nd_{0.3}$ |

Examples 10 to 17 and Comparative Examples 10 to 17 (Ammoxidation of propylene)

In Example 10, 60 cc of catalyst composition 1 was charged in a Vycol glass reaction tube having an inner diameter of 25 mm and having 14 steel nets of 10 (Tyler) mesh arranged at intervals of 1 cm. A gaseous mixture having a propylene content of 9% by volume (volume ratio of propylene: ammonia: oxygen: helium being 1:1.2:1.80:7.1) was flowed through the reaction tube at a flow rate of 4.06 cc/sec [0° C. under atmospheric pressure (N.T.P. conditions)]. The reaction pressure was maintained at atmospheric pressure, and the reaction temperature was maintained at 460° C. The results of the reaction were evaluated using three indices, namely, conversion of The reaction conditions and results of the ammoxidations using catalyst compositions 1 to 9 and 1' to 9' (exclusive of catalyst compositions 3 and 4') are shown in Table 3.

$$\text{Contact time (sec)} = \frac{V}{F \times (273 + T)/273}$$

wherein: V represents the amount (cc) of a catalyst;

F represents the flow rate (cc/sec) of the gaseous mixture of raw materials (in terms of the value under N.T.P. conditions); and T represents the reaction temperature (°C.).

TABLE 3

Ammoxidation of propylene
pressure: atmospheric pressure
gaseous mixture of raw materials:
$C_3H_6:NH_3:O_2:He = 1.0(9.0\%):1.2:1.8-1.9:Balance$

| | Catalyst composition No. | Temperature (°C.) | Contact time (Sec) | $O_2/C_3H_6$ | Conversion (C) (%) | Selectivity (S) (%) | Yield (Y) (%) |
|---|---|---|---|---|---|---|---|
| Example 10 | 1 | 460 | 5.5 | 1.80 | 98.3 | 85.8 | 84.3 |
| Example 11 | 2 | 460 | 5.5 | 1.80 | 98.3 | 85.5 | 84.0 |
| Comp. Ex. 10 | 1' | 460 | 5.5 | 1.80 | 98.7 | 84.3 | 83.2 |
| Comp. Ex. 11 | 2' | 460 | 5.5 | 1.80 | 98.8 | 84.0 | 83.0 |
| Comp. Ex. 12 | 3' | 460 | 5.5 | 1.83 | 99.2 | 82.3 | 81.6 |
| Example 12 | 4 | 460 | 5.5 | 1.80 | 98.5 | 85.4 | 84.1 |
| Example 13 | 5 | 460 | 5.5 | 1.80 | 98.7 | 85.3 | 84.2 |
| Comp. Ex. 13 | 5' | 460 | 5.5 | 1.83 | 99.3 | 82.6 | 82.0 |
| Example 14 | 6 | 430 | 5.0 | 1.90 | 98.2 | 85.0 | 83.5 |
| Comp. Ex. 14 | 6' | 430 | 5.0 | 1.90 | 98.5 | 83.9 | 82.6 |
| Comp. Ex. 15 | 7' | 430 | 5.0 | 1.90 | 98.8 | 82.1 | 81.1 |
| Example 15 | 7 | 430 | 5.0 | 1.90 | 98.5 | 84.3 | 83.0 |
| Example 16 | 8 | 430 | 5.0 | 1.90 | 98.6 | 84.8 | 83.6 |
| Comp. Example 16 | 8' | 430 | 5.0 | 1.90 | 98.9 | 82.4 | 81.5 |
| Example 17 | 9 | 430 | 5.0 | 1.90 | 98.7 | 84.9 | 83.8 |
| Comp. Ex. 17 | 9' | 430 | 5.0 | 1.90 | 99.1 | 81.9 | 81.2 |

Example 18
(Ammoxidation of isobutylene)

Using catalyst composition 3 and catalyst composition 4' (comparative) individually, ammoxidation reactions of isobutylene were conducted as follows. 60 cc of catalyst composition 3 was charged in the same reaction tube as used in the ammoxidation of propylene described above. The gaseous mixture having an isobutylene content of 7.5% by volume (volume ratio of isobutylene: ammonia: oxygen: water: helium being 1:1.2:2.0:1.8:7.33) was flowed through the tube at a flow rate of 4.63 cc/sec (in terms of the value under N.T.P. conditions). The reaction pressure was atmospheric pressure, and the reaction temperature was 435° C. The contact time was 5.0 seconds. Using catalyst composition 4' (comparative), substantially the same operation as mentioned above was conducted. The results of the reactions were evaluated using the conversion of isobutylene, the selectivity for methacrylonitrile and the methacrylonitrile yield as defined by substantially the same formulae as in the case of the ammoxidation of propylene, except that isobutylene is used in place of the propylene and methacrylonitrile is produced in place of the acrylonitrile. With respect to catalyst composition 3, the conversion of isobutylene was 99.3%, the selectivity for methacrylonitrile was 79.5% and the methacrylonitrile yield was 78.9%. With respect to catalyst composition 4', the conversion of isobutylene was 99.6%, the selectivity for methacrylonitrile was 76.3% and the methacrylonitrile yield was 76.0%.

Industrial Applicability

By use of the ammoxidation catalyst composition of the present invention in producing acrylonitrile from propylene, or methacrylonitrile from isobutylene, by ammoxidation of the propylene or of the isobutylene, acrylonitrile or methacrylonitrile can be produced with high selectivity.

I claim:

1. In an ammoxidation catalyst composition for use in producing acrylonitrile from propylene, or methacrylonitrile from isobutylene, by ammoxidation of said propylene or of said isobutylene, comprising an oxide catalyst and a silica carrier having said oxide catalyst supported thereon, wherein said silica carrier is present in an amount of from 40 to 60% by weight, based on the total weight of said oxide catalyst and said silica carrier, said oxide catalyst comprising oxides of molybdenum, bismuth, iron, and component A which is at least one element selected from potassium, rubidium and cesium, wherein bismuth, iron and component A are, respectively, present in amounts of from 0.1 to 6, from 0.1 to 8 and from 0.01 to 0.5 in terms of atomic ratios relative to twelve atoms of molybdenum, said ammoxidation catalyst composition being one which has been prepared by providing a slurry comprised of a silica sol and sources of component metallic elements of said oxide catalyst, and spray-drying said slurry, followed by calcination, the improvement in which said silica sol has an aluminum content of 0.04 or less in terms of an atomic ratio relative to 100 atoms of silicon.

2. The catalyst composition according to claim 1 wherein said silica sol has an aluminum content of 0.02 or less in terms of an atomic ratio relative to 100 atoms of silicon.

3. In a process for producing acrylonitrile or methacrylonitrile, which comprises reacting propylene with, or reacting isobutylene with ammonia and a molecular oxygen-containing gas in the gaseous phase in the presence of an ammoxidation catalyst composition comprising an oxide catalyst and a silica carrier having said oxide catalyst supported thereon, wherein said silica carrier is present in an amount of from 40 to 60% by weight, based on the total weight of said oxide catalyst and said silica carrier, said oxide catalyst comprising oxides of molybdenum, bismuth, iron, and component A which is at least one element selected from potassium, rubidium and cesium, wherein bismuth, iron and component A are, respectively, present in amounts of from 0.1 to 6, from 0.1 to 8 and from 0.01 to 0.5 in terms of atomic ratios relative to twelve atoms of molybdenum, said ammoxidation catalyst composition being one which has been prepared by providing a slurry comprised of a silica sol and sources of component metallic elements of said oxide catalyst, and spray-drying said slurry, followed by calcination, the improvement in which said silica sol has an aluminum content of 0.04 or less in terms of an atomic ratio relative to 100 atoms of silicon.

4. The process according to claim 3 wherein said silica sol has an aluminum content of 0.02 or less in terms of an atomic ratio relative to 100 atoms of silicon.

* * * * *

UNITED STATES PATENT AND TRADEMARK OFFICE
CERTIFICATE OF CORRECTION

PATENT NO. : 5,780,664

DATED : July 14, 1998

INVENTOR(S) : Kunitoshi Aoki

It is certified that error appears in the above-identified patent and that said Letters Patent is hereby corrected as shown below:

On the front page, please change "[22] PCT Filed: August 16, 1993" to read --[22] PCT Filed: August 16, 1994--.

Signed and Sealed this

Twenty-ninth Day of September, 1998

Attest:

BRUCE LEHMAN

*Attesting Officer*     *Commissioner of Patents and Trademarks*